(12) United States Patent
Wenzel (10) Patent No.: US 12,053,210 B2
(45) Date of Patent: Aug. 6, 2024

(54) PARTIALLY BLOCKED PEDICLE SCREW

(71) Applicant: Aesculap AG, Tuttlingen (DE)

(72) Inventor: Rudolf Wenzel, Nonnweiler-Primstal (DE)

(73) Assignee: Aesculap AG, Tuttlingen (DE)

( * ) Notice: Subject to any disclaimer, the term of this patent is extended or adjusted under 35 U.S.C. 154(b) by 258 days.

(21) Appl. No.: 17/619,732

(22) PCT Filed: Jun. 16, 2020

(86) PCT No.: PCT/EP2020/066605
§ 371 (c)(1),
(2) Date: Dec. 16, 2021

(87) PCT Pub. No.: WO2020/254310
PCT Pub. Date: Dec. 24, 2020

(65) Prior Publication Data
US 2022/0354545 A1    Nov. 10, 2022

(30) Foreign Application Priority Data

Jun. 17, 2019  (DE) .................... 10 2019 116 368.4

(51) Int. Cl.
*A61B 17/70*  (2006.01)
(52) U.S. Cl.
CPC ...... *A61B 17/7038* (2013.01); *A61B 17/7032* (2013.01)
(58) Field of Classification Search
CPC .............. A61B 17/7038; A61B 17/7032
USPC ....... 606/265, 267, 270, 272, 305, 308, 319, 606/320, 325
See application file for complete search history.

(56) References Cited

U.S. PATENT DOCUMENTS

| | | | |
|---|---|---|---|
| 5,989,254 | A | 11/1999 | Katz |
| 7,591,839 | B2 | 9/2009 | Biedermann et al. |
| 7,837,709 | B2 | 11/2010 | Dutoit et al. |
| 8,048,133 | B2 | 11/2011 | Biedermann et al. |

(Continued)

FOREIGN PATENT DOCUMENTS

| | | |
|---|---|---|
| CN | 1925804 A | 3/2007 |
| CN | 102525625 A | 7/2012 |

(Continued)

OTHER PUBLICATIONS

Search Report received in German Application No. 10 2019 116 374.9 dated Mar. 9, 2020, with translation, 11 pages.

(Continued)

*Primary Examiner* — Eduardo C Robert
*Assistant Examiner* — David C Comstock
(74) *Attorney, Agent, or Firm* — Christopher A. Rothe; Culhane PLLC (57) ABSTRACT

A pedicle screw with a receiving sleeve and a screw head includes a distal pivoting section that can be or is pivotally inserted into the receiving sleeve and a proximal holding section that can be or is inserted in a fixed position in the receiving sleeve, which are integrally connected to one another, in particular are manufactured in one piece, via at least one preferably elastically and/or plastically deformable web in such a way that they can be pivoted relative to one another about a pivot axis extending transversely to a longitudinal axis of a screw.

17 Claims, 4 Drawing Sheets

(56) References Cited

U.S. PATENT DOCUMENTS

| | | |
|---|---|---|
| 9,060,811 B2 | 6/2015 | Werner et al. |
| 9,138,261 B2 | 9/2015 | Di Lauro et al. |
| 9,492,209 B2 | 11/2016 | Biedermann et al. |
| 9,987,064 B2 | 6/2018 | Jensen |
| 2005/0143823 A1 | 6/2005 | Boyd et al. |
| 2005/0216003 A1* | 9/2005 | Biedermann ...... A61B 17/7035 606/279 |
| 2007/0093831 A1* | 4/2007 | Abdelgany ........ A61B 17/7038 606/250 |
| 2008/0119857 A1 | 5/2008 | Potash et al. |
| 2008/0147129 A1 | 6/2008 | Biedermann et al. |
| 2010/0036436 A1 | 2/2010 | Winslow et al. |
| 2010/0305621 A1 | 12/2010 | Wang et al. |
| 2011/0009911 A1 | 1/2011 | Hammill et al. |
| 2012/0053640 A1 | 3/2012 | Trieu |
| 2013/0023935 A1 | 1/2013 | Pham et al. |
| 2014/0343617 A1 | 11/2014 | Hannen |
| 2015/0282844 A1 | 10/2015 | Vedula et al. |
| 2017/0049484 A1* | 2/2017 | Leff .................. A61B 17/7037 |
| 2017/0079689 A1* | 3/2017 | Prevost ............. A61B 17/7037 |
| 2018/0132902 A1 | 5/2018 | Wu et al. |
| 2019/0069931 A1* | 3/2019 | Inceoglu ........... A61B 17/7032 |
| 2019/0223917 A1 | 7/2019 | Gray et al. |
| 2020/0146724 A1* | 5/2020 | Italiaie ............... A61B 17/7035 |

FOREIGN PATENT DOCUMENTS

| | | |
|---|---|---|
| CN | 104706405 A | 6/2015 |
| CN | 104902833 A | 9/2015 |
| EP | 1570796 A1 | 9/2005 |
| JP | 2008126066 A | 6/2008 |
| WO | 2014064249 A2 | 5/2014 |

OTHER PUBLICATIONS

Search Report received in International Application No. PCT/EP2020/066476 dated Oct. 23, 2020, with translation, 6 pages.
Written Opinion received in International Application No. PCT/EP2020/066476 dated Oct. 23, 2020, with translation, 15 pages.
Search Report received in German Application No. 10 2019 116 368.4 dated Mar. 9, 2020, with translation, 10 pages.
Search Report received in International Application No. PCT/EP2020/066605 dated Oct. 30, 2020, with translation, 5 pages.
Written Opinion received in International Application No. PCT/EP2020/066605 dated Oct. 30, 2020, with translation, 9 pages.
Office Action received in Japanese Application No. 2021-575498 dated Jun. 17, 2022, with translation, 5 pages.
Office Action received in Chinese Application No. 202080043769.5 dated Mar. 4, 2024, with translation, 16 pages.
Office Action received in Japanese Application No. 2021-575497 dated Nov. 9, 2023, with translation, 19 pages.

* cited by examiner

PARTIALLY BLOCKED PEDICLE SCREW

CROSS REFERENCE TO RELATED APPLICATIONS

This application is the United States national phase entry of International Application No. PCT/EP2020/066605, filed Jun. 16, 2020, and claims priority to German Application No. 10 2019 116 368.4, filed Jun. 17, 2019. The contents of International Application No. PCT/EP2020/066605 and German Application No. 10 2019 116 368.4 are incorporated by reference herein in their entireties.

FIELD

The present disclosure relates to a partially blocked pedicle screw (in short: screw) of the polyaxial type having a screw shaft and a screw head integrally connected thereto, which is rotatably and/or pivotably supported or received in a receiving sleeve (tulip).

BACKGROUND

Pedicle screws, in particular of the polyaxial type, are used in surgical procedures on the spinal column in order to fix the position of several vertebrae in relation to each other. The screws are each screwed into the pedicles of a vertebra and are connected via a connecting rod inserted into the screw heads or the tulips coupled to them. Depending on the application, screws with different degrees of freedom with regard to a relative movement between a tulip and a screw shaft are used. For example, for derotation of deformed spinal columns, screws are provided in which a pivot movement between the tulip and the screw shaft is blocked in the medial-lateral direction (i.e., in the lateral direction with respect to a spinal column or the associated human body or in a transverse plane), but is permitted in the cranial-caudal direction (i.e., in the longitudinal direction or height direction with respect to the spinal column or in a sagittal plane) for positioning during surgery. This is achieved by making the screw head non-circular, e.g. with lateral flattenings, and an inlay or insert inserted into the tulip for axial application of pressure to the screw head for fixing the relative position between the screw and the tulip is designed with corresponding lateral inner surfaces which come into contact with the flattenings on the screw head.

Such pedicle screws are implanted using a special instrument or instrument set, which is usually standardized for a number of different pedicle screws.

From the prior art, for example from US 2010/0305621 A1 and U.S. Pat. No. 9,138,261 B2, a polyaxial pedicle screw is known in each case whose round head, which is inserted in a receiving body, is at least partially flattened on two opposite sides, so that a bushing (inlay/insert for axial insertion in a tulip) arranged proximally to the head has two ear-shaped axial projections which form flat inner surfaces, are guided with these inner surfaces on the flattened sides of the head and permit pivoting of the screw shaft and head relative to the bushing only in a plane parallel to the flat inner surfaces. Part of the head of the pedicle screw may protrude radially beyond the flattened sides to provide additional screw diametrical support of the screw head on the receiving body. However, this limits an achievable pivoting angle and reduces the guiding surface. Furthermore, the flanges are slightly elastically deformable. Accordingly, high lateral forces may not be adequately supported.

U.S. Pat. No. 8,048,133 B2 discloses a polyaxial pedicle screw, whose round head is machined on two screw-diametrically opposite sides in order to form a screw-diametrically extending cylinder, which comes proximally into contact with a corresponding surface of a pressure element (inlay/insert) and together with this surface forms a kind of sliding bearing, which allows rotations about a cylinder axis and blocks rotations/pivot movements about other axes. However, this blocking of rotation or pivoting about other axes is likely to be insufficiently stable at high lateral forces and will lead to rapid wear or deterioration of the connection.

A further document, U.S. Pat. No. 5,989,254 A, shows a polyaxial pedicle screw with a spherical head in which a cylindrical saddle surface or a transverse slot with a saddle-shaped, longitudinally curved slot base is recessed to receive a connecting rod via which several pedicle screws can be connected. In the case where a tulip is placed over the screw head of the pedicle screw and a connecting rod is inserted transversely into the tulip, the saddle surface rolls off the connecting rod when the screw head is pivoted in the tulip about an axis running diametrically to the screw. Transverse forces are mainly transmitted via an outer surface of the connecting rod and side surfaces of the recess for the saddle surface, i.e. via a relatively short line contact. This construction is prospectively not sufficiently stable against high transverse forces.

In summary, known solutions have too many individual parts of the polyaxial pedicle screw and/or contain joints and are therefore complex to manufacture and to assemble. In particular, the internal geometry of the insert or insertion piece or retaining piece inserted proximally to the screw head within the tulip is often complex. This increases the manufacturing costs, among other things. Implantation of these screws may also require a separate set of instruments, which further increases the associated manufacturing costs due to lower quantities.

SUMMARY

The present invention is based on an object to reduce or avoid disadvantages of the prior art. In particular, a simple, stable pedicle screw with a screw head is to be provided that is pivotable within a receiving sleeve or tulip in one (single) screw-diametral direction and is fixed in position in another screw-diametral direction. Furthermore, with the present pedicle screw, in particular the instrumentation and set screws for fixing the screw, which should preferably be able to be loosened and tightened several times, of the same systems should be usable. In other words, the basic functions and the external geometry of the 'normal' (same system) polyaxial pedicle screw are to be retained.

The basic idea of the present invention is essentially to split the generally spherical screw head at its axially proximal apex, preferably in a V-shape, or to form it with a preferably V-shaped gap, and to connect the inlay, which is known per se from the prior art (which exerts an axial pressure on the screw head within a tulip and thus braces the head and the tulip with/against each other), to the pedicle screw, preferably in an integral manner, via a preferably plate-shaped web (plate/spring tongue), by (integrally) fixing the web in the axial direction of the screw to the inlay and in the gap base to the screw head. In this way, the web may swing back and forth resiliently within the gap (wherein the flanks of the gap serve as end stop surfaces) and thus the inlay can be moved (pendulum-like) along the circumference of the screw head.

In other words, the object is solved by a polyaxial pedicle screw with a receiving sleeve or tulip and a screw head, which has a distal pivoting section (ball head of the pedicle screw) pivotably (or rotatably) inserted or insertable in the receiving sleeve/tulip, and a proximal holding section (inlay) inserted or insertable in a fixed position in the receiving sleeve/tulip. These two sections are integrally connected to each other, in particular manufactured in one piece, via at least one web/plate/tongue in such a way that they are pivotable relative to each other about a pivot axis extending transversely to a longitudinal axis of the screw (i.e. screw diametral). Preferably, the web may be elastically and/or plastically deformable in order to enable the pivoting section and the holding section to pivot.

In other words, in the pedicle screw according to the invention, the holding section (inlay) and the pivoting section (screw head) are integrally manufactured (or joined by welding/soldering/adhesive bonding), wherein the pivotability is ensured by a connecting section or web which, at least in sections, is sufficiently narrow in order to be deformed/bent with a reasonable amount of force and in a sufficiently large area for use in spinal surgery.

A titanium alloy is provided as the preferred material for such a pedicle screw. This simplifies both production and commissioning of the individual parts and assembly of the pedicle screw. Consequently, manufacturing costs can be reduced.

The web may be connected to the holding section (inlay/insert) and the pivoting section (screw head) at various points and may have various shapes, for example straight, loop-shaped or s-shaped. Depending on the shape and arrangement, the web may have different properties and may, for example, be uniformly bendable, bendable according to a certain gradient, or only bendable at at least one defined point. Similarly, the holding section (inlay) may have different shapes in order to prevent twisting or slipping in the receiving sleeve/tulip, wherein the holding section (inlay) is fixed in the longitudinal direction of the screw, if applicable, only by screwing a connecting/transverse rod and a set screw into the receiving sleeve/tulip. Preferably, the outer geometry of the holding section (inlay) corresponds to an outer geometry of an insert/inlay of a standard pedicle screw of the same system. In order to ensure pivotability between the receiving sleeve/tulip and the pivoting section (screw head), either the screw head and/or the receiving sleeve may be concavely and convexly rounded at a contact area thereof.

It is advantageous if the at least one web is a material section which is arranged between two slots or wedges (i.e., slot-shaped or wedge-shaped recesses) recessed in the pivoting section (screw head) or in the holding section (inlay/insert). This ensures uniform pivoting of the two components.

It has proven useful if one end of the at least one web, at which it is integrally connected to the holding section (inlay/insert) or the pivoting section (screw head), serves as a pivoted or bending joint. If applicable, the web may, for example, have a constriction or a reduced cross-section at the point at which it is intended to bend/tilt in order to generate the pivoting, which provides a predetermined bending point. This is possible in particular since the joint (film hinge) formed in this way is fixed in the installation position using a set screw when the pedicle screw is implanted and only has to be intact and movable up to this point. Accordingly, breaking of the web due to permanent load is not to be feared. If slots or wedges are provided in the pivoting section (screw head) or in the holding section (inlay/insert) as described above, this pivoted joint is preferably provided at the end of the web which is located at the bottom of these slots (slot base) or wedges.

It is expedient if the flanks of the slots or wedges serve as a stop for limiting pivoting of the pivoting section and the holding section. This advantageously limits the pivoting of the holding section (inlay/insert) and the pivoting section (screw head), which in particular preserves the pivoted joint if it is formed between the slots or wedges. Furthermore, this makes it possible to place the receiving sleeve/tulip in a defined stop position during an operation. The slots or wedges should allow a pivoting angle of at least +/−22°, preferably at least +/−30°. That means, if the wedges or slots are symmetrical, the angles between the longitudinal axis of the screw and the stops formed by the flanks are each at least 22°, preferably at least 30°. This ensures the necessary mobility of the pedicle screw.

Preferably, the slots or wedges and/or the two gaps separating the pivoting section (screw head) and the holding section (inlay/insert) are made or machined by a separation process, preferably by wire cutting. In other words, the shape is modified, without dividing it, by machining wedges in such a way that the holding section (inlay/insert), which assumes the function of an insert of a standard pedicle screw, can be moved while deforming the remaining webs. Accordingly, the pedicle screw head may be easily manufactured in one piece without excessively increasing costs. Furthermore, high accuracy is achieved, in particular since surfaces on both sides of the slot fit together (sufficiently) accurately without additional finishing.

According to a preferred embodiment of the invention, the at least one web extends straight. In this case, the at least one web is relatively stiff and can thus help to support correspondingly high lateral loads, thereby helping to prevent pivoting about an axis transverse to the pivot axis. Furthermore, the at least one web is particularly simple and thus inexpensive to manufacture. Alternatively, the at least one web may also be corrugated. This may provide advantages in terms of improved mobility of the web or easier deformation during movement of the holding section (and of the receiving sleeve).

Preferably, the pivoting section (screw head) has a lateral cylinder surface proximally, and the holding section (inlay/insert) has a corresponding lateral inner cylinder surface distally. Alternatively, the pivoting section (screw head) has a lateral inner cylinder surface proximally, and the holding section (inlay/insert) has a corresponding lateral cylinder surface distally. This complementary shape is achieved in particular by the insertion of a slot and allows a pivoting/rotating movement of the holding section (inlay/insert) and the pivoting section (screw head) relative to each other. In particular, it is provided that the end of the web serving as the pivoted joint is located on a longitudinal axis of the lateral cylinder surface to ensure this rotation/pivoting. Depending on the width of the slot and the load applied (in particular with a corrugated web), these two surfaces can come into contact and serve as a guide geometry. In principle, however, the slot may also be made sufficiently large so that the two surfaces are clearly spaced apart, since a guide geometry can basically be dispensed with in the pedicle screw according to the invention. In both cases, the holding section (inlay/insert) and the pivoting section (screw head) are designed in such a way that the lateral cylinder surface and the lateral inner cylinder surface at least partially overlap in each pivoting position. In this way, a guiding or supporting function (in particular in the installed state) can be ensured, if required. Furthermore, this always shields the wedges or slots so that no foreign bodies or the like can be introduced therein and possibly block the mobility of the screw head.

Furthermore, it has proven advantageous if the pivoting section (screw head) is laterally and proximally widened in such a way that it at least partially forms a (main) cylinder extending in the longitudinal direction of the screw in order to be supported on an inner surface of the receiving sleeve/tulip in the direction of the pivot axis. This particularly stable design allows high lateral loads of up to 500N to be supported in order to block pivoting about an axis transverse to the pivot axis. Preferably, both this cylindrical (clamping) surface and the at least one web support the side loads. In this case, it is useful to provide recesses in the receiving sleeve/tulip (which preferably corresponds to the base or 'body' of a standard pedicle screw) which preferably form a substantially rectangular or square space so that the pedicle screw is movable within the receiving sleeve/tulip. In particular, it is necessary that the recesses are formed in such a way that the cylindrical part (the main cylinder) of the pivoting section has space therein in any pivoting position.

Preferably, the pedicle screw described above allows pivoting in a cranial-caudal direction and preferably blocks pivoting in a medial-lateral direction. In particular, cranial-caudal movement of the screw head under lateral loads of at least 500N is to be prevented. These directional specifications refer to an intended installation situation of the pedicle screw during an operation. I.e., when the pedicle screw is inserted into the spinal column, the screw shaft and the receiving sleeve should be movable relative to each other in the cranial-caudal direction, i.e., in a sagittal plane, and should be fixed in position in the lateral-medial direction, i.e., in a transverse plane.

It is also expedient if a channel running through the holding section (inlay/insert) and into the pivoting section (screw head) is provided in order to form a tool receptacle for implanting the pedicle screw. If applicable, the web is thereby divided so that a narrower web remains on both sides of the channel.

BRIEF DESCRIPTION OF THE DRAWING FIGURES

The present invention is described hereinafter with reference to preferred embodiments. However, these are merely for illustrative purposes and are not intended to limit the scope of protection of the present invention.

DETAILED DESCRIPTION

Figure 1:
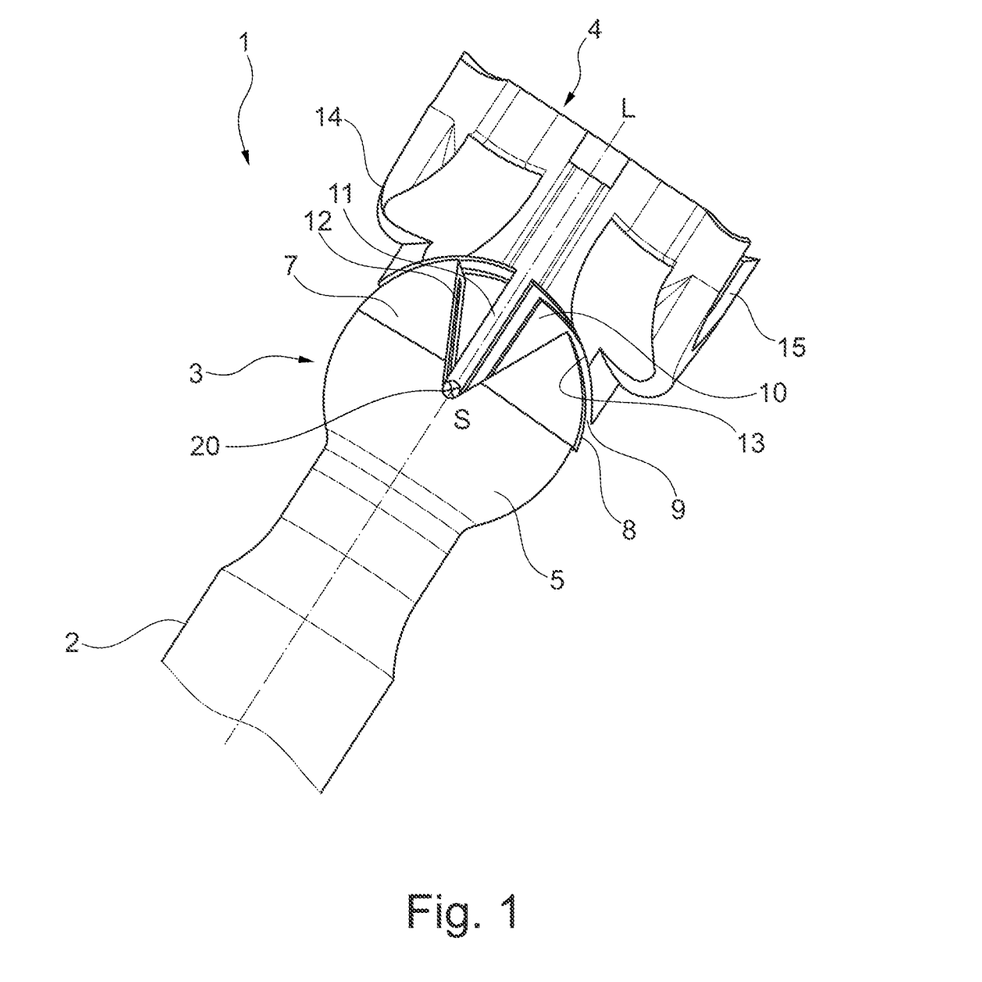
FIG. 1 shows a head of a pedicle screw according to a first embodiment of the present disclosure.

FIG. 1 shows a screw head 1 of a first embodiment of a pedicle screw according to the invention. A screw shaft 2 formed integrally or in one piece with the screw head 1 and extending distally from the screw head 1 is shown here only in rough outline.

The screw head 1 is made in two parts and has a distal pivoting section 3 (corresponding to the actual screw head or ball head of the pedicle screw at the proximal end of the screw shaft 2) and a proximal holding section 4 (corresponding to the insert/inlay inside a tulip). The pivoting section 3 is round, preferably spherical, at least at its distal end 5 (preferably at least its distal half) connected to the screw shaft 2. In the fully assembled state, this round end is received in a receiving sleeve or tulip 6 (shown in FIG. 2) and enables the screw head 1 to be rotatably mounted in the receiving sleeve 6. A proximal end 7 of the screw head 1 (preferably approximately a proximal half) at least partially forms a so-called 'Steinmetz body'. I.e., the proximal end 7 is formed by two intersecting cylinders: a main cylinder extending from the distal end 5 in the proximal direction (in the longitudinal direction of the screw), and an auxiliary cylinder extending in the direction of a pivot axis S and providing a lateral cylinder surface or guiding surface 8 for guiding a pivot movement between the pivoting section 3 and the holding section 4. The auxiliary cylinder, in particular the guiding surface 8, is manufactured by introducing two diametrically opposite gaps 9 into the initially undivided screw head 1, for example by wire cutting.

In addition, starting from the proximal lateral surface of the auxiliary cylinder, two symmetrical wedge-shaped recesses (wedges) 10 are formed centrally in the screw head 1, for example together with the gaps 9 by wire cutting. These wedges 10 are open in the proximal direction so as to be connected in each case to one of the gaps 9, and extend in the distal direction in such a way that they converge towards the pivot axis S, in particular towards a center of the round screw head 1, and that a web 11, or in this example two webs 11, remains or remain between the two wedges 10. That is, each web 11 extends from the pivot axis S straight in the proximal longitudinal direction L of the screw so that on either side of the web 11, the wedge-shaped recesses or wedges 10 are recessed in the screw head 1, wherein these preferably pass completely through the proximal end 7 and extend into the distal end 5. Flanks 12 of the wedges 10 opposite each web 11 represent stops for limiting the pivot movement. In order to enable pivoting of at least +/−22°, preferably at least or up to +/−30°, the wedges 10 accordingly have an angle of at least +/−22°, preferably at least or up to +/−30°. It should be noted that in this example two diametrically opposite webs 11 are provided, since in the illustrated pedicle screw, a central channel, for example for injecting bone cement and/or for receiving a screw instrument for implanting the screw, is provided which separates the two webs 11 from each other. Alternatively, however, only a single continuous web 11 may be provided.

At a proximal end, the webs 11 are integrally connected to the holding section 4. On both sides of the webs 11, a receiving surface (lateral inner cylinder surface) 13, shaped like the inner lateral surface of a cylinder, is formed along the gaps 9 opposite the guiding surface 8 of the pivoting section 3 at a distal end of the holding section 4. The contour of the receiving surface follows that of the guiding surface 8 in such a way that the gaps 9 have a constant width. This means that the guiding surface 8 and the receiving surface 13 are produced by introducing the gaps 9 into the initially undivided screw head 1 in order to separate the pivoting section 3 and the holding section 4 from each other. Accordingly, the holding section 4 is at least partially cylindrical on its distal side in order to continue the main cylinder in the longitudinal direction L of the screw. Preferably, the gaps 9 are as narrow as possible so that the guiding surface 8 and the receiving surface 13 can interact, if applicable, in the manner of a plain bearing.

Proximal to the cylindrical distal side, the holding section 4 forms two screw-diametrically opposite bulges 14, which are essentially part of a cylinder extending transversely to the pivot axis S, and subsequently extend in the proximal direction. These bulges 14 are provided to be received and held in a fixed position in a corresponding seat 15 of the receiving sleeve 6 (see FIG. 2). Furthermore, the holding section 4 is opened in a U-shape along the bulges 14 to provide standardized saddle surfaces 16 for receiving a rod for connecting a plurality of pedicle screws. Thus, the pedicle screw according to the invention can be used with system-associated instruments or accessories like such a rod. The same applies to the design of the receiving sleeve 6, more precisely, its outer contours as well as a thread embedded therein for set screws for clamping the rod. It should furthermore be noted that the arrangement of the bulges 14 with respect to the web 11 determines the direction of the pivot movement when the pedicle screw is implanted, since the rod usually runs essentially parallel to the spinal column of a patient. In this example, the rod would run transversely to the pivot axis S, which is why the pivot movement of the pedicle screw head 1 and shaft 2 is enabled in the sagittal plane of the patient and a pivot movement in the transverse plane is blocked by the webs 11 and by a subsequently described interaction of the screw head 1 and the receiving sleeve 6.

Figure 2:
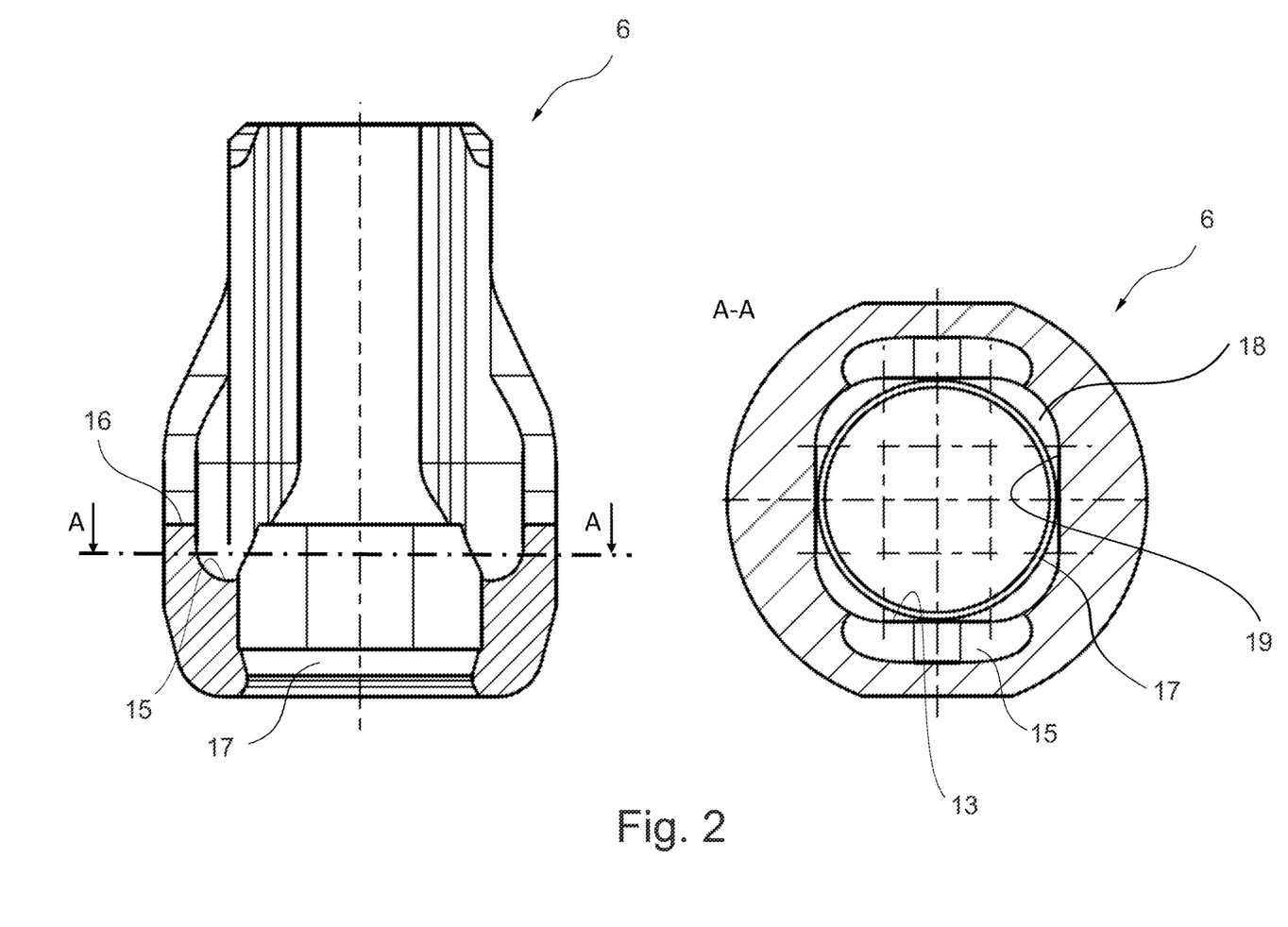
FIG. 2 shows a longitudinal section and a cross-sectional view of a receiving sleeve according to the first or second embodiment of the present disclosure.

In the longitudinal section of the receiving sleeve 6 shown on the left in FIG. 2, in addition to the seat 15 and the saddle surfaces 16 already described, it can also be clearly seen that an inner diameter of the receiving sleeve 6 narrows at its distal end via a conical receiving surface 17. This receiving surface 17 serves for the pivotable or rotatable mounting or reception of the round distal end 5 of the screw head 1. In the cross-section of the receiving sleeve 6 shown on the right in FIG. 2, a substantially square space 18 created in the receiving sleeve is also shown which is introduced into the receiving sleeve 6 directly proximal to the receiving surface 17 and whose side walls 19 extend substantially tangentially to the receiving surface 17. These side walls 19 are adapted to fit/abut against the main cylinder of the proximal end 7 of the pivoting section 3 and to bear thereon in order to block a pivot movement transverse to the pivot axis S.

Figure 3:
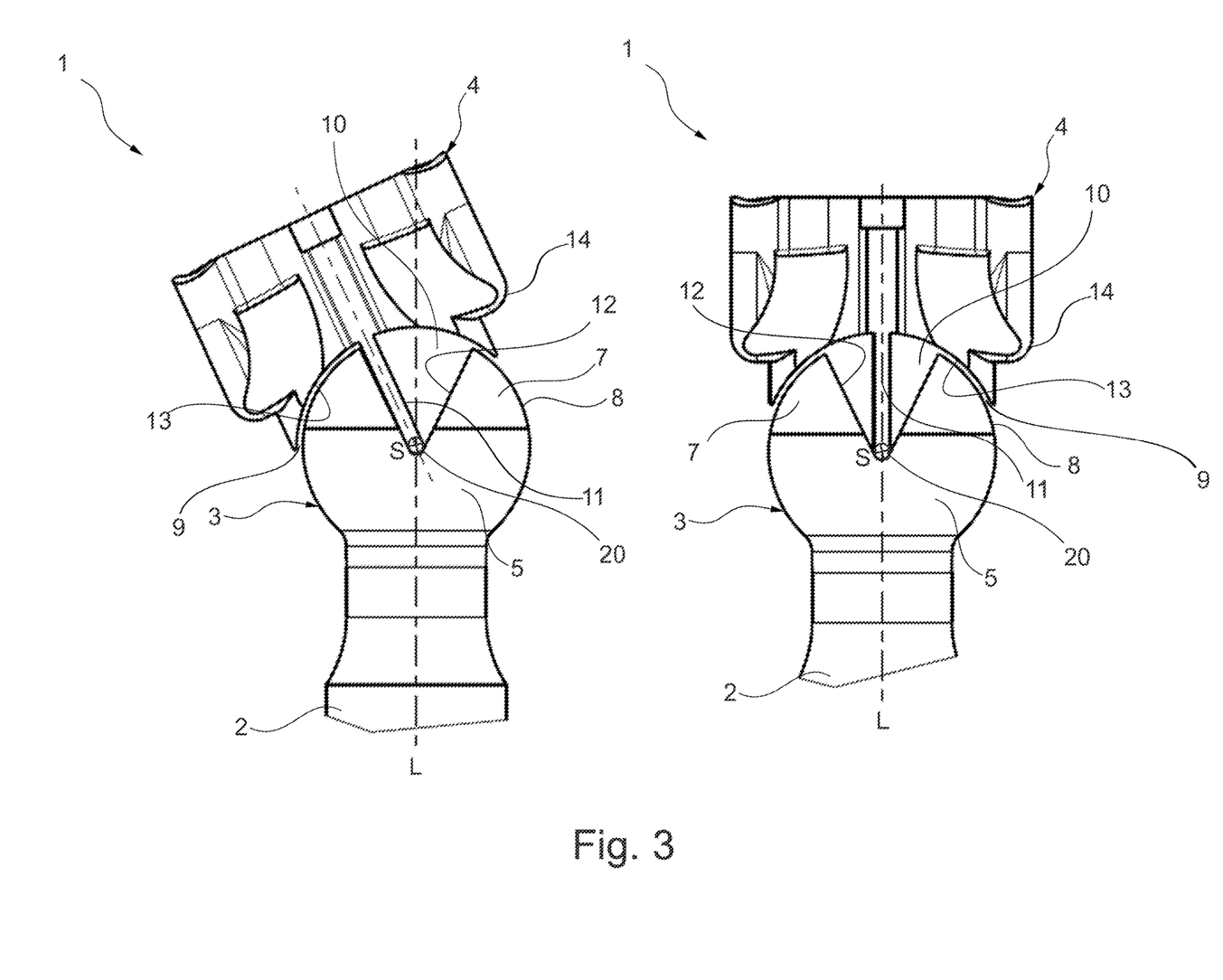
FIG. 3 illustrates the principle of operation of the pedicle screw according to the first embodiment.

FIG. 3 serves to illustrate the principle of operation of the pedicle screw according to the invention. The illustration of the screw head 1 on the right essentially corresponds to the illustration in FIG. 1, in which the pivoting section 3 and the holding section 4 are not restricted against each other (i.e., a longitudinal axis of the holding section 4 corresponds to the longitudinal direction L of the screw). It can also be seen that the guiding surface 8 and the receiving surface 13 overlap in the longitudinal direction of the screw. On the left in FIG. 3, the screw head 1 is shown in a maximum pivoted state of the pivoting section 3 and of the holding section 4. The guiding surface 8 and the receiving surface 13 extend far enough that they overlap each other in the longitudinal direction of the screw even in this maximum pivoted state and thus provide guidance during the complete pivoting movement. In this state, the web 11 is kinked at its distal end, i.e. at least elastically, possibly also plastically, deformed. The distal end of the at least one web 11 thus acts as a kind of pivoted joint 20 about which each web 11 tilts about the pivot axis S. Furthermore, in the maximum pivoted state, the web 11 is in contact with the flank 12 of one of the wedges 10, thereby limiting a maximum pivoting or tilting angle. This wedge 10 is consequently closed by the deformation of the web 11 and the opposite wedge 10 is approximately twice as wide.

Figure 4:
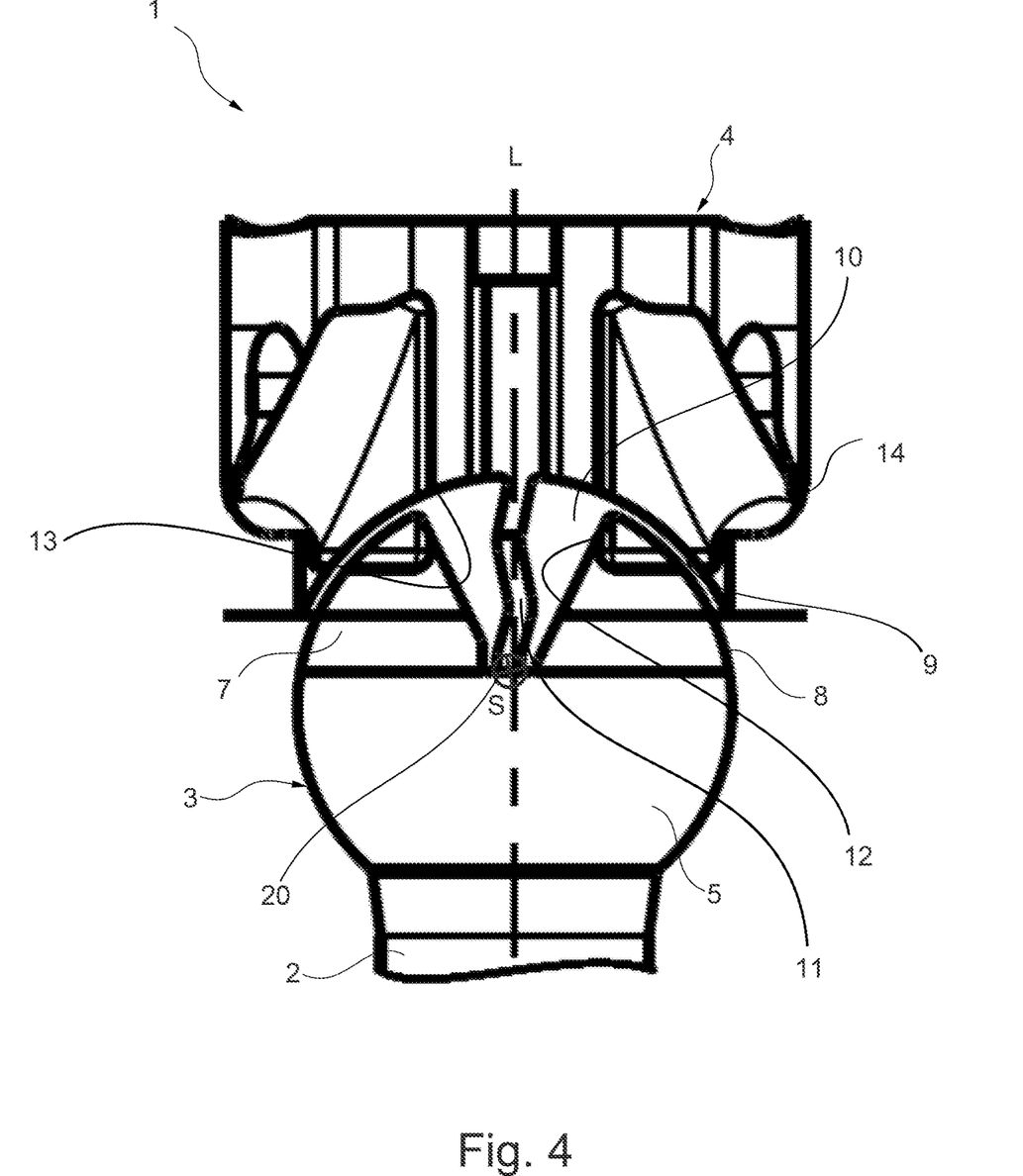
FIG. 4 shows a head of a pedicle screw according to a second embodiment of the present disclosure.

FIG. 4 is a representation of the screw head 1 according to a further embodiment of the present disclosure. This embodiment is substantially the same as the first embodiment, and therefore only differences between the two embodiments will be explained below, wherein the same reference signs are used for features corresponding to each other. The pedicle screw according to the second embodiment shown here has, in contrast to the straight web 11 of the first embodiment, a web 11 which is corrugated. The corrugated web 11 is more easily deformable, which means that orienting the receiving sleeve 6 via the holding section 4 and the web 11 requires less force on the part of the user. Accordingly, less force is transmitted to the tissue via the screw shaft 2, and handling during surgery is simplified. On the other hand, the web 11 is also more easily deformable in relation to a deformation transverse to the pivot axis S, which is why transverse loads have to be absorbed more via the main cylinder of the proximal end 7 of the pivoting section 3 compared to the first embodiment.

The invention claimed is:

1. A pedicle screw with a receiving sleeve and a screw head,
wherein the screw head has a pivoting section which is pivotably insertable or inserted in the receiving sleeve and a holding section of the screw head which is insertable or is inserted in a fixed position in the receiving sleeve, wherein the pivoting section and the holding section are integrally connected to each other via at least one web, in such a way that the pivoting section and the holding section are pivotable relative to each other about a pivot axis extending transversely to a longitudinal axis of the screw, wherein the at least one web is a material section arranged between two slots or wedges recessed in the pivoting section or in the holding section; and
wherein the at least one web is corrugated.

2. The pedicle screw according to claim 1, wherein an end of the at least one web is a pivoted joint at which the at least one web is integrally connected to the holding section or the pivoting section.

3. The pedicle screw according to claim 2, wherein the pivoting section has a lateral cylinder surface proximally, and the proximal holding section has a corresponding lateral inner cylinder surface distally, or the pivoting section has a lateral inner cylinder surface proximally, and the proximal holding section has a corresponding lateral cylinder surface distally, which correspondingly at least partially overlap in each pivoting position.

4. The pedicle screw of claim 3, wherein the end of the at least one web is located on a longitudinal axis of the lateral cylinder surface.

5. The pedicle screw according to claim 1, wherein flanks of the slots or wedges serve as a stop for limiting pivoting of the pivoting section and the holding section.

6. The pedicle screw according to claim 1, wherein the slots or wedges allow a pivoting angle of at least +/−22°.

7. The pedicle screw according to claim 1, wherein the slots or wedges and/or two gaps separating the pivoting section and the holding section are machined out by a separation process.

8. The pedicle screw according to claim 1, wherein the pivoting section is laterally and proximally widened in such a way that the pivoting section at least partially forms a cylinder extending in a longitudinal direction of the screw in order to be supported on an inner surface of the receiving sleeve in a direction of the pivot axis.

9. The pedicle screw according to claim 1, wherein recesses are provided in the receiving sleeve so that the pedicle screw is movable within the receiving sleeve.

10. The pedicle screw according to claim 1, wherein pivoting is enabled in the cranial-caudal direction.

11. The pedicle screw according to claim 10, wherein pivoting is blocked in the medial-lateral direction.

12. The pedicle screw according to claim 1, wherein the pivoting section and the holding section are manufactured in one piece.

13. A pedicle screw with a receiving sleeve and a screw head,
- wherein the screw head has a pivoting section which is pivotably insertable or inserted in the receiving sleeve and a holding section of the screw head which is insertable or is inserted in a fixed position in the receiving sleeve, wherein the pivoting section and the holding section are integrally connected to each other via at least one web, in such a way that the pivoting section and the holding section are pivotable relative to each other about a pivot axis extending transversely to a longitudinal axis of the screw, wherein the at least one web is a material section arranged between two slots or wedges recessed in the pivoting section or in the holding section;
- wherein an end of the at least one web is a pivoted joint at which the at least one web is integrally connected to the holding section or the pivoting section; and
- wherein the pivoting section has a lateral cylinder surface proximally, and the proximal holding section has a corresponding lateral inner cylinder surface distally, or the pivoting section has a lateral inner cylinder surface proximally, and the proximal holding section has a corresponding lateral cylinder surface distally, which correspondingly at least partially overlap in each pivoting position.

14. The pedicle screw of claim 13, wherein the end of the at least one web is located on a longitudinal axis of the lateral cylinder surface.

15. A pedicle screw with a receiving sleeve and a screw head,
- wherein the screw head has a pivoting section which is pivotably insertable or inserted in the receiving sleeve and a holding section of the screw head which is insertable or is inserted in a fixed position in the receiving sleeve, wherein the pivoting section and the holding section are integrally connected to each other via at least one web, in such a way that the pivoting section and the holding section are pivotable relative to each other about a pivot axis extending transversely to a longitudinal axis of the screw, wherein the at least one web is a material section arranged between two slots or wedges recessed in the pivoting section or in the holding section; and
- wherein the pivoting section is laterally and proximally widened in such a way that the pivoting section at least partially forms a cylinder extending in a longitudinal direction of the screw in order to be supported on an inner surface of the receiving sleeve in a direction of the pivot axis.

16. A pedicle screw with a receiving sleeve and a screw head,
- wherein the screw head has a pivoting section which is pivotably insertable or inserted in the receiving sleeve and a holding section of the screw head which is insertable or is inserted in a fixed position in the receiving sleeve, wherein the pivoting section and the holding section are integrally connected to each other via at least one web, in such a way that the pivoting section and the holding section are pivotable relative to each other about a pivot axis extending transversely to a longitudinal axis of the screw, wherein the at least one web is a material section arranged between two slots or wedges recessed in the pivoting section or in the holding section; and
- wherein pivoting is enabled in the cranial-caudal direction.

17. The pedicle screw according to claim 16, wherein pivoting is blocked in the medial-lateral direction.

* * * * *